United States Patent [19]

Barber

[11] Patent Number: 5,346,462
[45] Date of Patent: Sep. 13, 1994

[54] ADJUSTABLE TENSION FINGER OR TOE SPLINT

[75] Inventor: Lois M. Barber, Pismo Beach, Calif.

[73] Assignee: LMB Hand Rehab Products, Inc., San Luis Obispo, Calif.

[21] Appl. No.: 7,337

[22] Filed: Jan. 21, 1993

[51] Int. Cl.⁵ ............................................. A61F 5/00
[52] U.S. Cl. .................................. 602/22; 602/30; 602/5; 128/880
[58] Field of Search .................. 602/5, 6, 12, 21, 22, 602/23, 30, 62, 64; 128/26, 879, 880

[56] References Cited

U.S. PATENT DOCUMENTS

| | | | |
|---|---|---|---|
| 826,515 | 7/1906 | Litch | 602/30 |
| 1,055,810 | 3/1913 | Scholl | 602/30 |
| 1,144,103 | 6/1915 | Brant | 602/22 |
| 1,227,700 | 5/1917 | Tucker | 602/21 |
| 1,471,948 | 10/1923 | Cox et al. | 602/22 |
| 1,633,037 | 6/1927 | Rood | 128/880 |
| 2,074,113 | 3/1937 | Hovey | 128/880 |
| 2,682,869 | 7/1954 | Papp | 602/21 |
| 3,039,460 | 6/1962 | Chandler | 602/22 |
| 4,103,682 | 8/1978 | Franzl | 602/22 |
| 4,384,571 | 5/1983 | Nuzzo et al. | 602/22 |

FOREIGN PATENT DOCUMENTS 1503798  8/1989  U.S.S.R. ............................ 602/22

*Primary Examiner*—Richard J. Apley
*Assistant Examiner*—Linda C. Dvorak
*Attorney, Agent, or Firm*—George F. Bethel; Patience K. Bethel

[57] ABSTRACT

An adjustable tension and adjustable compression splint for one or more joints on a finger or a toe formed of a strip of elastic, stretchy material which is cooperatively joined with a narrow pocket containing a dynamic extension strut or stay or a static malleable position strut or stay.

12 Claims, 3 Drawing Sheets

ADJUSTABLE TENSION FINGER OR TOE SPLINT

BACKGROUND OF THE INVENTION

FIELD OF THE INVENTION

This invention relates to the field of finger and toe splints and especially to an adjustable tension finger or toe splint having adjustable compression.

DESCRIPTION OF THE PRIOR ART

Many finger splints are available in the prior art for supporting a finger or toe. These have mainly comprised initially a piece of wood such as a tongue depressor coupled with adhesive tape to immobilize the finger. Other finger splints provide a stiffening means with other dynamic and static supports but mainly these splints suffer from the drawbacks of not being capable of accommodating swelling of the finger such as would be experienced during many injuries. Also, these finger splints are not readily adapted for use over a bandaged finger nor are they capable of the versatility of static and/or dynamic extension capabilities.

Other desirable features which are not found in prior art splints are breathability, washability, or the ability to be used on a total finger or on a PIP (proximal interphalangeal) or DIP (distal interphalangeal) joint alone. Also, most of these splints are very difficult or complicated to apply.

In an effort to overcome the deficiencies of the prior art splints, a finger or toe splint has been invented which will accommodate swelling by adjustment of a unique compression cover. This finger or toe splint can be used for static positioning in various angles from straight to bent and can be easily modified by manually bending. Because of its particular features, the finger or toe splint of the invention can be worn over a light bandage.

If desired this novel finger or toe splint can be used for dynamic tension or, dynamic extension. Moreover, the tension can be modified by manually hyperextending a spring strut or stay.

In addition, this novel finger or toe splint can be made in varying sizes so that it can be used on an entire finger or toe or be limited to the PIP or DIP joints alone by use of a smaller length.

Because of the unique features of the finger or toe splint of the invention, it is easy to put on and take off and the materials of which it is made permit machine washability and good ventilation.

SUMMARY OF THE INVENTION

The adjustable tension and adjustable compression finger or toe splint of the invention is comprised of a length of elastic, stretchy material which is cooperatively interlaced with a foam support which holds either a dynamic extension strut or stay or a static malleable position strut or stay.

According to one embodiment, the stretchy material is separate from the foam support and stay which are united by a lacing means. According to another embodiment, the stretchy material can be stitched or otherwise attached to the foam cushioning material. The stretchy material and the cushioning material or stay and can be provided with attachment means such as a brushed material and hooks arrangement whereby the splint can be wrapped around a finger and adjustably attached by means of areas of interlocking hooks and areas of brushed material.

By varying the length of the splint, it can be used for single joint application or for multiple joint application on a finger, a thumb, or a toe. When used on a thumb, the splint is preferably used with a wrist strap to deter slippage.

The splint is also suitable for use on a toe if provided in a small size and length.

Depending on the desired use, the splint can be used with the stay contacting the dorsal or volar part of the finger. However, it is most preferred to have the stay in volar contact with a finger or toe.

Another advantage of the splint of the invention is that the tips of the fingers can be left free for limited use thereof.

Other types of adjustable attachments means are contemplated which can be substituted for the lacing and hooked and brush material attachments to provide an adjustable compression which can be established upon one occasion and subsequently changed without difficulty.

As used herein and in the appended claims the terms:
"volar" refers to the palm or underside of a finger;
"dorsal" refers to the backside of a finger;
"IP" refers to interphalangeal;
"MP" refers to metacarpophalangeal;
"CM" refers to carpometacarpal;
"PIP" refers to proximal interphalangeal;
"DIP" refers to distal interphalangeal;
"distal" means farthest from the center of the body;
"proximal" means closest to the center of the body.

BRIEF DESCRIPTION OF THE DRAWINGS

The invention will be more readily understood by reference to the description below taken in conjunction with the accompanying drawings wherein.

DETAILED DESCRIPTION OF THE INVENTION

Figure 1:
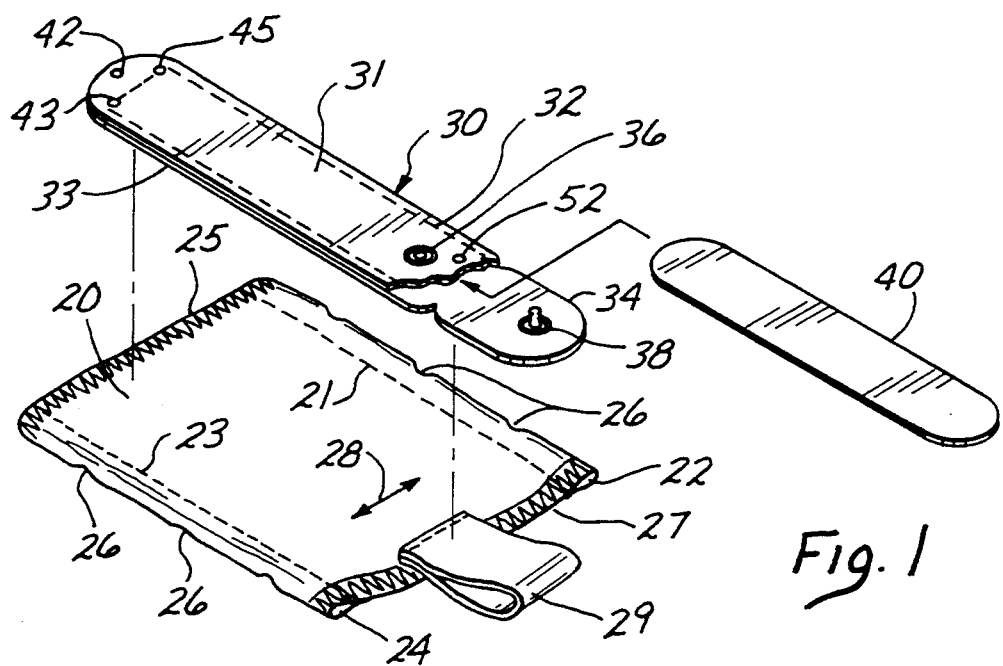
FIG. 1 shows an exploded perspective view of the parts of the preferred embodiment of the finger or toe splint of the invention.
Figure 2:
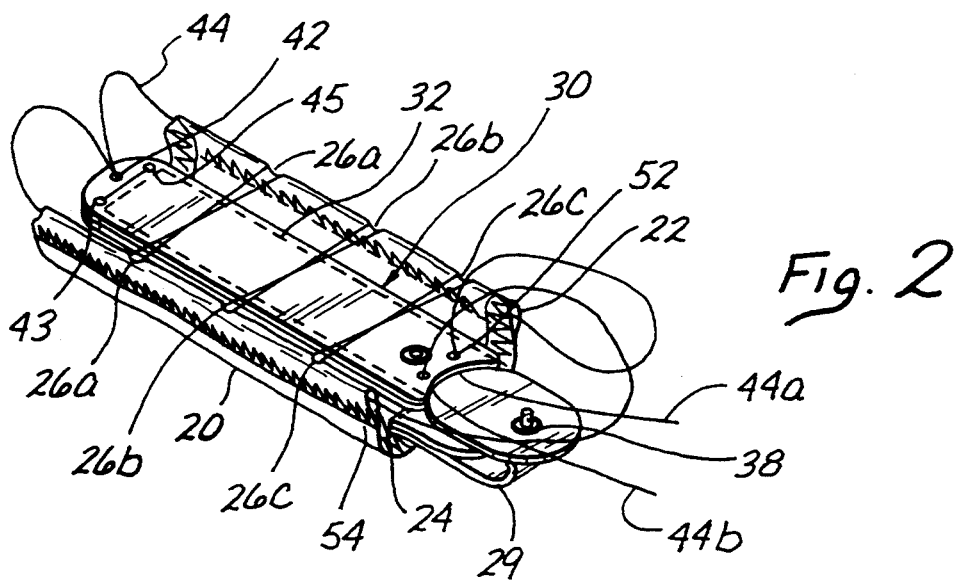
FIG. 2 shows a perspective view of the partially assembled parts of the preferred splint with the lacing material included.

Referring now to FIGS. 1 and 2, it can be seen that the splint includes a length of material or fabric 20 generally longer than its width. The dimensions of the material depend on the joints to be treated, the nature of the injury, and the presence of a bandage.

Preferably the material 20 is provided with widthwise stretch as indicated at 28 on material 20. This stretchiness is in the direction of the manner of surrounding a finger or toe to be splinted. The material 20 can also be stretchy all over but this is less preferred. The provision of a stretchy material provides even, balanced compression along the finger or toe to be splinted.

If desired, the elastic material 20 can have a taper along its length to conform generally to the decreasing diameter of a finger or toe.

The material 20 has opposed edge regions 21 and 23 which are rolled over and stitched down to form interior channels 22 and 24 along the length of the material 20. The opposite edge regions 25 and 27 which are disposed between stitched down edge regions 22 and 24 are overcast to reinforce the fabric and to prevent fraying.

Figure 8:
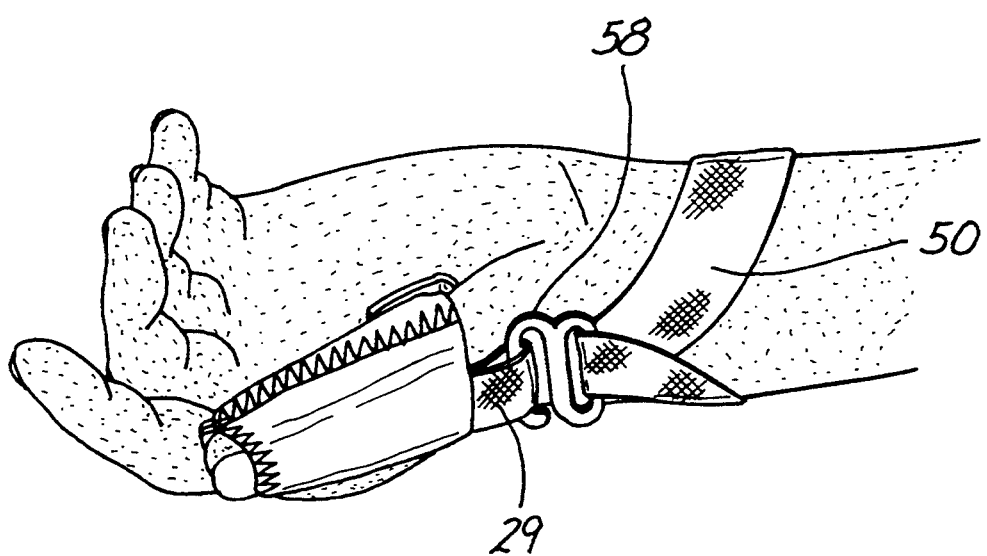
FIG. 8 shows the splint on a user's thumb in conjunction with a wrist strap.

Within the interior channels 22 and 24 are disposed a plurality of openings 26 for receipt of a length of string or cord 44. A loop 29 at the proximal end of the splint provides a grasping means to aid in placing the splint over a finger or toe to be splinted. In addition, the loop 29 can be used in conjunction with a hook 58 on a wrist strap 50 as shown in FIG. 8 to prevent slipping off of a user's thumb.

A narrow pocket 30 shown in FIG. 1 is comprised of a top layer 31 and a slightly longer bottom layer 33. The top layer 31 is provided with half of a snap closure at its proximal end. The longer bottom layer extends beyond the top layer 31 to form a tab 34 which is provided with the other half of the snap closure 38.

Preferably, the two layers are formed of cushioning material such as a foam or most preferably a fabric backed foam. However, this is not a requirement. The stay can have no cushioning or cushioning material can be adhered to the stay. Preferably, the two layers 31 and 33 are stitched around three sides as indicated at 32 leaving an opening at the proximal end for insertion of a strut or stay 40. The distal end of pocket 30 is provided with openings 42, 43, and 45 through layers 31 and 33 for reception of a string or cord 44. The proximal end of top layer 31 is also provided with openings 52 and 54 for cord 44.

The strut or stay 40 which is received within pocket 30 can be either static or dynamic depending upon the desired treatment. If a static stay is used, it is preferably formed of a malleable material which can be manually bent to the desired angle for treatment.

As detailed in FIG. 2, the material 20 and the pocket 30 are held together by means of the cording 44. To assemble the splint, the two ends of the cord 44a and 44b are inserted respectively into openings 45 and 43 and then inserted together into opening 42 from the opposite side.

Figure 3:
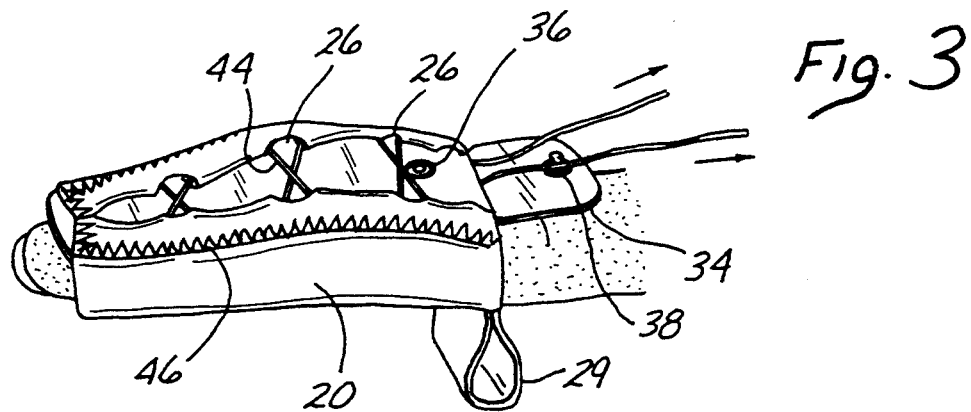
FIG. 3 shows the splint on a user's finger with the stay or strut in the volar position and with the lacing material tightened to the desired compression.
Figure 4:
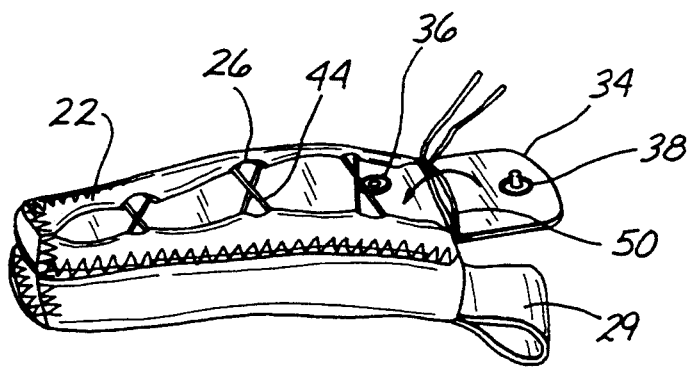
FIG. 4 shows the splint of the invention with the lacing material wrapped around a snap tab.

The respective ends 44a and 44b are then threaded into the distal end of edge channel 22 and 24 respectively. The cord ends 44a and 44b are then brought out of openings 26a and crossed over for reinsertion into openings 26b and 26c in the manner of lacing as shown in FIGS. 2 and 3. The cord ends 44a and 44b are then brought together at the proximal end of the splint where they exit edge channels 22 and 24 respectively. Here, the cord ends 44a and 44b are inserted respectively into openings 52 and 54 in top layer 31.

Figure 7:
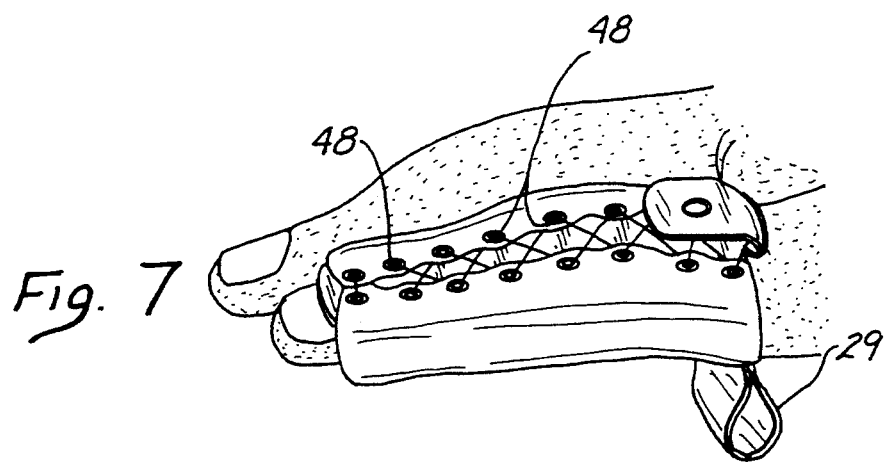
FIG. 7 shows an alternate embodiment using eyelets and lacing with the splint placed with the stay on the dorsal side of a finger.

The above manner of lacing is preferred for this embodiment. However, the invention is not limited by the manner of attachment of the stay or strut 40 to the fabric material 20. For example, FIG. 7 shows eyelets 48 in place of the edge channels 22 and 24 and openings 26. Also, the cord 44 is preferably inelastic, elastic cording can be used as well.

In the most preferred embodiment as shown in FIGS. 1–6, the cord ends 44a and 44b after being laced as above described can be tightened by pulling on the cord ends 44a and 44b. Loosening can be achieved by pulling apart the cross lacing. When the desired compression for an individual finger or toe has been achieved, the cords can be secured. This is conveniently effected by winding the cord ends 44a and 44b around tab 34 and then closing the snap closure parts 36 and 38.

In place of the snap closure, a button can be provided for winding around the cord ends 44a and 44b. Loosening can then be easily achieved by unwinding the cord ends 44a and 44b from the button and loosening the lacing.

While the preferred embodiment shows the tab 34 at the proximal end of the splint, the tab 34 can, if desired, be placed at the distal end of the splint, although this is less preferred.

If desired, the securement of the cord ends 44a and 44b can be done while the splint is on a finger or toe. As an alternative, the desired compression can be measured on a finger or toe, then the splint removed for closing the snap parts 36 and 38. The splint can then be slipped onto the finger to be treated. The stretchiness of the material 20 makes this convenient.

A particularly advantageous feature of the splint is the snug fit which is made possible by the stretchy material. This feature, when coupled with the adjustable securement of the strut and cushioning to the stretchy material provides even compression along the length of a finger or toe to be splinted. The stretchy feature also permits limited movement of the finger in the event that the dynamic stay is employed in the splint.

While the lacing with edge channels and eyelets have been shown, other methods for joining the material 20 to the strut 40 are also contemplated. For example, the strut 40 or pocket 30 and the material 20 can be provided with areas of hooks and areas of brushed material.

Also, straps having areas of hooks or areas of brushed material can be attached to the pocket 30 and/or to the material 20. In this manner, the compression of the splint around a finger can be adjusted as needed to accommodate swelling and the like. When the swelling has subsided, the splint can then be easily readjusted to a smaller diameter by means of the straps.

Similarly, while the splint is shown as having separate parts, it is contemplated that the stretchy material could be stitched or otherwise attached to the strut or pocket on one or both sides and provided with means for adjusting the compression around a finger or toe to be splinted.

The splint is also useful for splinting a thumb. With limited movement of a splinted thumb, there is a tendency for the splint to slip. Therefore, as shown in FIG. 8, the splint when used on a thumb is preferably used in conjunction with a hooked wrist strap. As shown, a hook 58 on wrist strap 50 is inserted into loop 29 of the splint. When the splint is on a user's thumb, the wrist strap 50 counteracts the tendency of the splint to slip off of a user's thumb. Use of the wrist strap 50 is not necessary for splinting a thumb, but it has been found that better results can be obtained with its use.

The splint as above described can be used either with the strut in volar or dorsal contact with a finger or toe. In general, since most swelling takes place on the dorsal part of a finger, the volar contact is most preferred. It is more comfortable to have the stretchy material in contact with the swelling.

Figure 5:
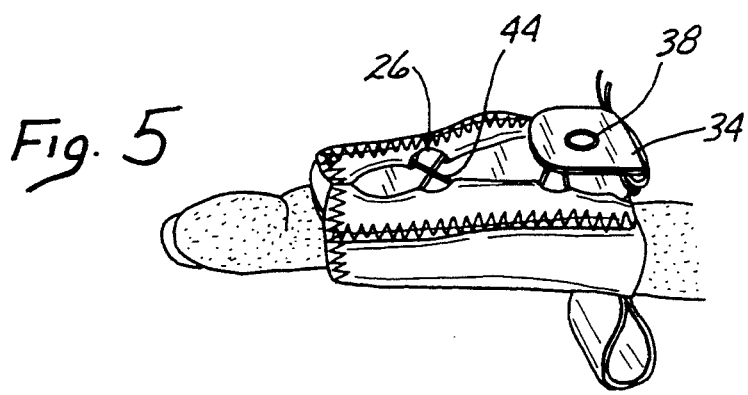
FIG. 5 shows the splint of the invention with the stay in the dorsal position with the snap tab closed over the wrapped lace winding to secure the lacing material at the desired compression.
Figure 6:
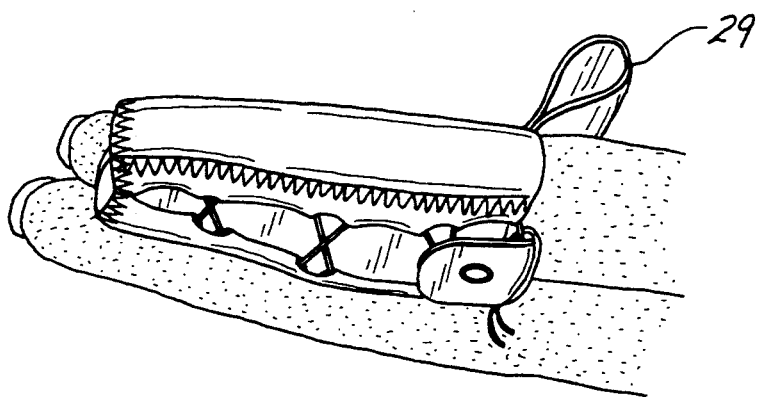
FIG. 6 shows the splint on a finger with the stay placed on the volar side of a finger.

Also, the length of the splint can be made shorter as shown in FIG. 5 in order to treat a single joint while keeping the remaining joint free to move.

Similarly, the width of the splint can be varied to accommodate different sized fingers and toes and to accommodate a large bandage.

Various modifications of the invention are contemplated and can be resorted to by those skilled in the art without departing from the spirit and scope of the invention as defined by the following claims.

I claim:

1. An adjustable tension and adjustable compression finger or toe splint comprising:
   a first part comprising a strip of material for lengthwise dorsal or volar contact with a finger or toe;
   a second part comprising a stiffening means for dorsal or volar contact with a finger or toe to be splinted; and,
   means for securing said stiffening means to said strip of material for adjustable compression along the length of the splint while surrounding a finger or toe to be splinted;
   wherein said strip is formed of elastic material and is provided with lengthwise opposed edge portions defining interior channels along two opposed edges and with openings spaced along the length of said channels and cord means for insertion within said lengthwise channels and wherein said stiffening means is provided with at least one opening for receiving a portion of said cord means for adjusting tension around a finger or toe.

2. A splint according to claim 1 wherein said cord means is elastic.

3. A splint according to claim 1 wherein said stiffening means comprises a stay which is disposed within a narrow pocket having means thereon for temporary securement of said cord means.

4. A splint according to claim 3 wherein said stay is selected from dynamic, flexible stays and static, stiff stays.

5. A splint according to claim 3 wherein said narrow pocket is comprised of cushioning material having an opening at one end for receiving said stay and being further provided with cord retaining means for receiving said cord means and for retaining said cord means in a preadjusted compression state.

6. A splint according to claim 5 wherein said cord retaining means comprises a tab for winding said cord means therearound, said tab having a snap closure.

7. A splint according to 5 wherein said cord retaining means comprises a button for winding said cord means therearound.

8. A splint according to claim 7 wherein cushioning material is used to surround said stay.

9. A splint according to claim 8 wherein said stay is formed of a bendable material.

10. A splint according to claim 1 wherein said strip of elastic material is tapered along its length to conform to the decreasing diameter of a finger or toe to be splinted.

11. A splint according to claim 1 wherein said splint has an attachment means for attachment to a wrist strap.

12. An adjustable tension and adjustable compression finger or toe splint comprising:
    a first part comprising a strip of material for lengthwise dorsal or volar contact with a finger or toe;
    a second part comprising a stiffening means for dorsal or volar contact with a finger or toe to be splinted; and,
    means for securing said stiffening means to said strip of material for adjustable compression along the length of the splint while surrounding a finger or toe to be splinted;
    wherein said strip is provided with lengthwise edge portions having opposed eyelets for receiving cord means and wherein said stiffening means is provided with an opening for receiving cord means for adjusting the compression around a finger or toe.

* * * * *